(12) United States Patent
Tomchik et al.

(10) Patent No.: US 11,990,244 B2
(45) Date of Patent: *May 21, 2024

(54) SYSTEM AND METHOD PROVIDING RISK RELATIONSHIP TRANSACTION AUTOMATION IN ACCORDANCE WITH MEDICAL CONDITION CODE

(71) Applicant: HARTFORD FIRE INSURANCE COMPANY, Hartford, CT (US)

(72) Inventors: Gary S. Tomchik, Houston, TX (US); Oksana Kamyshin, Spring, TX (US); Keren Shemesh, West Hartford, CT (US); Lori Katherine Walters, West Simsbury, CT (US); Chris C. Kuo, Grendale, NY (US); Seda V. Remus, Issaquah, WA (US); Dean M. Mazzotta, North Granby, CT (US); Shashank Aditya Adepu, Charlotte, NC (US)

(73) Assignee: HARTFORD FIRE INSURANCE COMPANY, Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,000

(22) Filed: Jan. 18, 2023

(65) Prior Publication Data

US 2023/0154622 A1    May 18, 2023

Related U.S. Application Data

(63) Continuation of application No. 16/849,437, filed on Apr. 15, 2020, now Pat. No. 11,594,334.

(51) Int. Cl.
| | | |
|---|---|---|
| *G16H 50/30* | (2018.01) | |
| *G16H 50/20* | (2018.01) | |
| *G16H 70/60* | (2018.01) | |

(52) U.S. Cl.
CPC ............. *G16H 50/30* (2018.01); *G16H 50/20* (2018.01); *G16H 70/60* (2018.01)

(58) Field of Classification Search
CPC ........ G16H 50/30; G16H 50/20; G16H 70/60; G16H 15/00; G16H 40/20; G06Q 40/08
See application file for complete search history.

(56) References Cited

U.S. PATENT DOCUMENTS

| | | | |
|---|---|---|---|
| 6,692,436 B1 * | 2/2004 | Bluth .................... | A61B 5/411 128/920 |
| 2003/0135397 A1 * | 7/2003 | Halow .................. | G06Q 30/04 705/4 |

(Continued)

OTHER PUBLICATIONS

A systems model for community injury prevention; Russell, Mary T.. ProQuest Dissertations and Theses, ProQuest Dissertations Publishing. (1997) (Year: 1997).*

*Primary Examiner* — Amber A Misiaszek
(74) *Attorney, Agent, or Firm* — Buckley, Maschoff & Talwalkar LLC (57) ABSTRACT

A system to provide a risk relationship transaction automation tool via a back-end application computer server of an enterprise. The system may include a risk relationship data store that contains electronic records representing transactions associated with requested resource allocations between the enterprise and a plurality of entities. The server may receive an indication of a selected requested resource allocation transaction and retrieve, from the risk relationship data store, the electronic record associated with the selected requested resource allocation transaction. The server may then execute a medical code decision model. According to some embodiments, the system may also support a graphical interactive user interface display via a distributed communication network, the interactive user interface display providing resource allocation transaction data.

18 Claims, 11 Drawing Sheets

(56) References Cited

U.S. PATENT DOCUMENTS

| | | | |
|---|---|---|---|
| 2005/0108063 A1* | 5/2005 | Madill, Jr. | G06Q 40/08 705/4 |
| 2007/0162308 A1* | 7/2007 | Peters | G06Q 10/06 705/2 |
| 2013/0144656 A1* | 6/2013 | Peak | G06Q 40/08 705/4 |
| 2017/0270611 A1* | 9/2017 | Boundy | G06Q 40/08 |

* cited by examiner

SYSTEM AND METHOD PROVIDING RISK RELATIONSHIP TRANSACTION AUTOMATION IN ACCORDANCE WITH MEDICAL CONDITION CODE

CROSS REFERENCE TO RELATED APPLICATION

This is a continuation of U.S. patent application Ser. No. 16/849,437 entitled "SYSTEM AND METHOD PROVIDING RISK RELATIONSHIP TRANSACTION AUTOMATION IN ACCORDANCE WITH MEDICAL CONDITION CODE," filed on Apr. 15, 2020, the entire contents of which are incorporated herein by reference for all purposes.

BACKGROUND

It may be advantageous to analyze the risks and resource allocations associated with multiple systems and/or entities. For example, it might be advantageous to understand particular amounts of risk and allocations and the impact that such risks and allocations may have had on past (and, potentially, future) performance. Moreover, an enterprise might want to facilitate understanding and reaction to requests for allocations of resources (e.g., transactions associated with the risk relationship)—and a review of such requests may be an important part of this process. The breadth and depth of information associated with resource request transactions, often over an extended period of time, can overwhelm such a review process. That is, manually examining and understanding these types of risks and allocations associated with risk relationships can be a complicated, time consuming, and error-prone task, especially when there are a substantial number of inter-related systems, entities, characteristics impacting resource allocations, and/or other factors involved in the analysis.

It would be desirable to provide systems and methods for a risk relationship transaction automation tool that allow faster, more accurate results as compared to traditional approaches.

SUMMARY OF THE INVENTION

According to some embodiments, systems, methods, apparatus, computer program code and means are provided for a risk relationship transaction automation tool that allow faster, more accurate results as compared to traditional approaches and that allows for flexibility and effectiveness when acting on those results. In some embodiments, a system may provide a risk relationship transaction automation tool via a back-end application computer server of an enterprise. The system may include a risk relationship data store that contains electronic records representing transactions associated with requested resource allocations between the enterprise and a plurality of entities. The server may receive an indication of a selected requested resource allocation transaction and retrieve, from the risk relationship data store, the electronic record associated with the selected requested resource allocation transaction. The server may then execute a medical code decision model. According to some embodiments, the system may also support a graphical interactive user interface display via a distributed communication network, the interactive user interface display providing resource allocation transaction data.

Some embodiments comprise: means for receiving, at a back-end application computer server, an indication of a selected requested resource allocation transaction between the enterprise and an entity; means for retrieving, from a risk relationship data store, an electronic record associated with the selected requested resource allocation transaction, including at least one code representing a medical condition, wherein the risk relationship data store contains electronic records that represent a plurality of transactions associated with requested resource allocations between the enterprise and a plurality of entities, each electronic record including an electronic record identifier and the at least one code representing a medical condition; means for executing a predictive model and business rules based on the at least one code to generate a likelihood of acceptance score for the selected requested resource allocation transaction; and means for assigning the selected requested resource allocation transaction to a recommendation category based on the likelihood of acceptance score.

In some embodiments, a communication device associated with a back-end application computer server exchanges information with remote devices in connection with an interactive graphical user interface. The information may be exchanged, for example, via public and/or proprietary communication networks.

A technical effect of some embodiments of the invention is an improved and computerized way to provide a risk relationship transaction automation tool that allows faster, more accurate results as compared to traditional approaches. With these and other advantages and features that will become hereinafter apparent, a more complete understanding of the nature of the invention can be obtained by referring to the following detailed description and to the drawings appended hereto.

DETAILED DESCRIPTION

The present invention provides significant technical improvements to facilitate electronic messaging and dynamic data processing. The present invention is directed to more than merely a computer implementation of a routine or conventional activity previously known in the industry as it significantly advances the technical efficiency, access, and/or accuracy of communications between devices by implementing a specific new method and system as defined herein. The present invention is a specific advancement in the area of electronic risk analysis and/or resource allocation by providing benefits in data accuracy, data availability, and data integrity and such advances are not merely a longstanding commercial practice. The present invention provides improvement beyond a mere generic computer implementation as it involves the processing and conversion of significant amounts of data in a new beneficial manner as well as the interaction of a variety of specialized client and/or third-party systems, networks, and subsystems. For example, in the present invention information may be processed, updated, and analyzed via a back-end-end application server to accurately improve the analysis of risk, the allocation of resources, and/or the exchange of information, thus improving the overall efficiency of the system associated with message storage requirements and/or bandwidth considerations (e.g., by reducing the number of messages that need to be transmitted via a network). Moreover, embodiments associated with collecting accurate information might further improve risk values, predictions of risk values, allocations of resources, electronic record routing and signal generation, etc.

Figure 1:
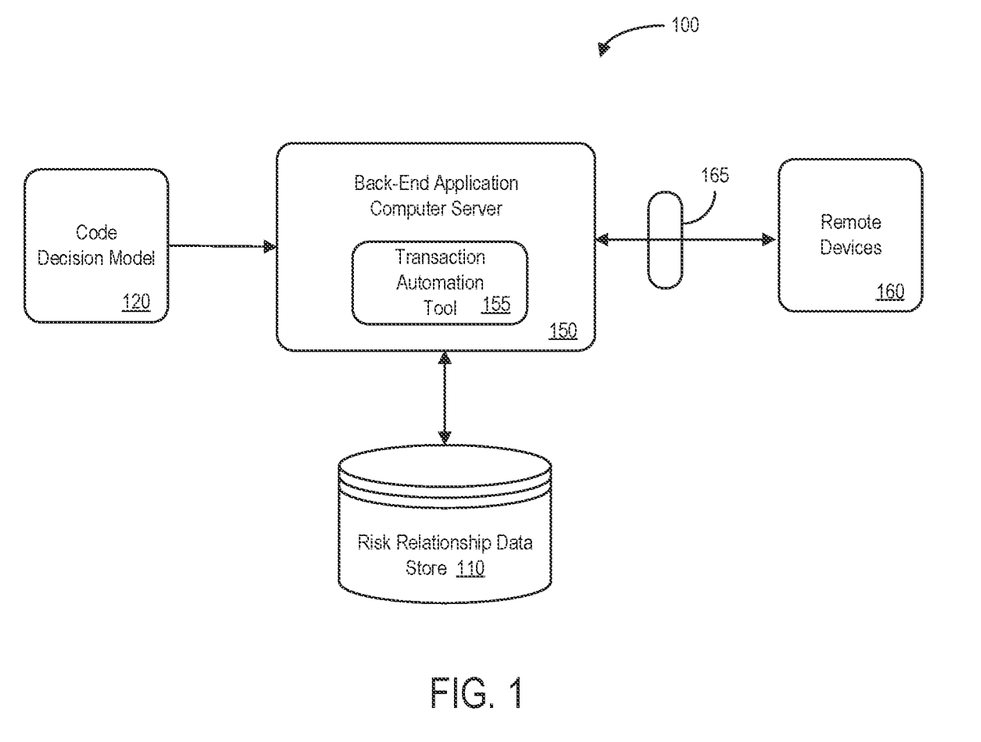
FIG. 1 is a high-level block diagram of a system in accordance with some embodiments.

For example, FIG. 1 is a high-level block diagram of a system 100 according to some embodiments of the present invention. In particular, the system 100 includes a back-end application computer 150 server that may access information in a risk relationship data store 110 (e.g., storing a set of electronic records that represent transactions associated with requests for an allocation of resources, each record including, for example, one or more risk relationship identifiers, requested resource allocation identifiers, transaction values, etc.). The back-end application computer server 150 may also retrieve information from a code decision model 120 in connection with a transaction automation tool 155. According to some embodiments, the system 100 further applies machine learning, artificial intelligence algorithms, business logic, and/or other models to the electronic records. The back-end application computer server 150 may also exchange information with a remote device 160 (e.g., via communication port 165 that might include a firewall). According to some embodiments, an interactive graphical user interface platform of the back-end application computer server 150 (and, in some cases, third-party data) may facilitate the display of information associated with the transaction automation tool 155 via one or more remote computers (e.g., to enable a manual review of a resource allocation transaction) and/or the remote device 160. For example, the remote device 160 may receive updated information (e.g., information about a medical condition) from the back-end application computer server 150. Based on the updated information, a user may review the data from the risk relationship data store 110 and take informed actions in response to request transactions. Note that the back-end application computer server 150 and/or any of the other devices and methods described herein might be associated with a cloud-based environment and/or a third party, such as a vendor that performs a service for an enterprise.

The back-end application computer server 150 and/or the other elements of the system 100 might be, for example, associated with a Personal Computer ("PC"), laptop computer, smartphone, an enterprise server, a server farm, and/or a database or similar storage devices. According to some embodiments, an "automated" back-end application computer server 150 (and/or other elements of the system 100) may facilitate updates of electronic records in the risk relationship data store 110. As used herein, the term "automated" may refer to, for example, actions that can be performed with little (or no) intervention by a human.

As used herein, devices, including those associated with the back-end application computer server 150 and any other device described herein may exchange information via any communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The back-end application computer server 150 may store information into and/or retrieve information from the risk relationship data store 110. The risk relationship data store 110 might, for example, store electronic records representing a plurality of resource allocation request transactions, each electronic record having a risk relationship identifier, a transaction identifier, a set of attribute values including one or more resource values, etc. The risk relationship data store 110 may also contain information about prior and current interactions with entities, including those associated with the remote devices 160. The risk relationship data store 110 may be locally stored or reside remote from the back-end application computer server 150. As will be described further below, the risk relationship data store 110 may be used by the back-end application computer server 150 in connection with an interactive user interface to provide information about transactions and/or the transaction automation tool 155. Although a single back-end application computer server 150 is shown in FIG. 1, any number of such devices may be included. Moreover, various devices described herein might be combined according to embodiments of the present invention. For example, in some embodiments, the back-end application computer server 150 and the risk relationship data store 110 might be co-located and/or may comprise a single apparatus.

According to some embodiments, the system 100 may provide a dashboard view of insurance claim transaction files. This might help, for example, an insurance claims handler quickly determine key claim information about an injured worker, insured, and/or treatment provider along with data that might help a claim handler decide how to proceed with respect to the transaction.

Figure 2:
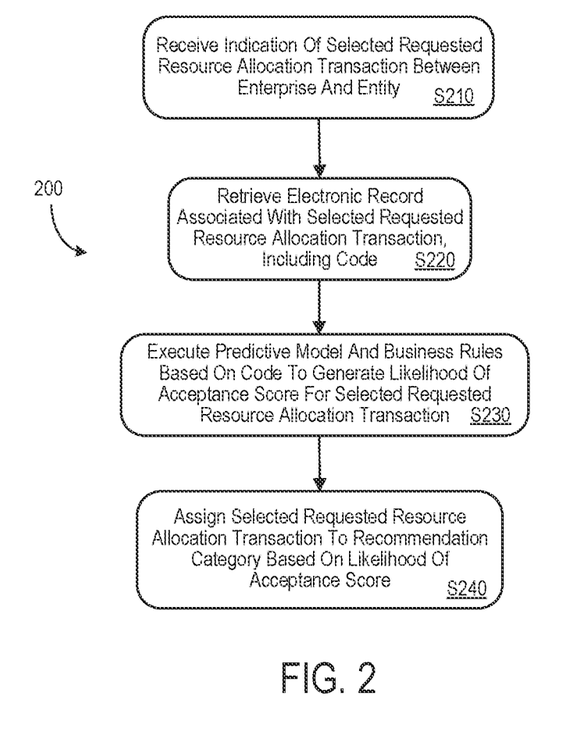
FIG. 2 illustrates a code decision model method according to some embodiments of the present invention.

Note that the system 100 of FIG. 1 is provided only as an example, and embodiments may be associated with additional elements or components. According to some embodiments, the elements of the system 100 automatically transmit information associated with an interactive user interface display over a distributed communication network. FIG. 2 illustrates a method 200 that might be performed by some or all of the elements of the system 100 described with respect to FIG. 1, or any other system, according to some embodiments of the present invention. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At S210, a back-end application computer server (e.g., associated with an enterprise) may receive an indication of a requested resource allocation transaction between the enterprise and an entity. For example, an operator or administrator associated with the enterprise might select a resource allocation request from a list of pending resource allocation requests. According to some embodiments, the operator may search for requests based on an entity name, a request type, a date associated with the request, etc. At S220, the back-end application computer server may retrieve, from a risk relationship data store, an electronic record associated with the selected requested resource allocation transaction, including at least one code representing a medical condition. The code might, for example, be associated with International Statistical Classification of Diseases ("ICD") and Related Health Problems codes generated by the World Health Organization. For example, an ICD code of "S91.339A" might indicate a "puncture wound without foreign body unspecified foot—initial encounter." There are approximately 70,000 ICD codes, with each digit of the ICD providing a granular level of detail about the diagnosis.

At S230, the system may execute a predictive model and business rules based on the at least one code to generate a likelihood of acceptance score for the selected requested resource allocation transaction. According to some embodiments, the selected requested resource allocation transaction is associated with a workers' compensation insurance claim. Moreover, the predictive model may be associated with data science model scoring. For example, the data science model scoring might utilize a hierarchical variable clustering process and unsupervised learning based on historical insurance claim results.

At S240, the system may assign the selected requested resource allocation transaction to a recommendation category based on the likelihood of acceptance score. According to some embodiments, the assigned recommendation category might represent automatic approval of the code or an indication that an injury is likely related to the code. Similarly, the assigned recommendation category might instead indicate that the system was unable to recommend the code for approval or that the code is unlikely related to an injury.

In some embodiments, a transaction workflow may be automatically routed to a claims handler in accordance with the recommendation category. Moreover, a communication port coupled to a back-end application computer server may facilitate a transmission of data with a remote device (e.g., a claims handler device) to support a graphical interactive user interface display via a distributed communication network. The interactive user interface display might, for example, provide resource allocation data including the likelihood of acceptance score and the recommendation category.

In this way, the likelihood of acceptance score may be used to categorize some ICD codes as being likely to be approved (and, thus, require less manual review). The ICD decision model may mitigate leakage in workers' compensation medical claim payout by driving accurate, consistent, and timely decisions related to diagnoses. Note that workers' compensation claim adjusters may be tasked with making decisions regarding the relatedness of diagnosis codes (e.g., ICD codes) to an underlying workplace injury. An ICD code might be accepted, denied, or placed under investigation for further review. The time and accuracy associated with each ICD decision can vary based on handler experience, ICD, and claim complexity. The decision making process may often include a review of medical documents, the nature of the injury, other related attributes of the claim, etc., and some decisions may require a higher level of clinical expertise.

Figure 3:
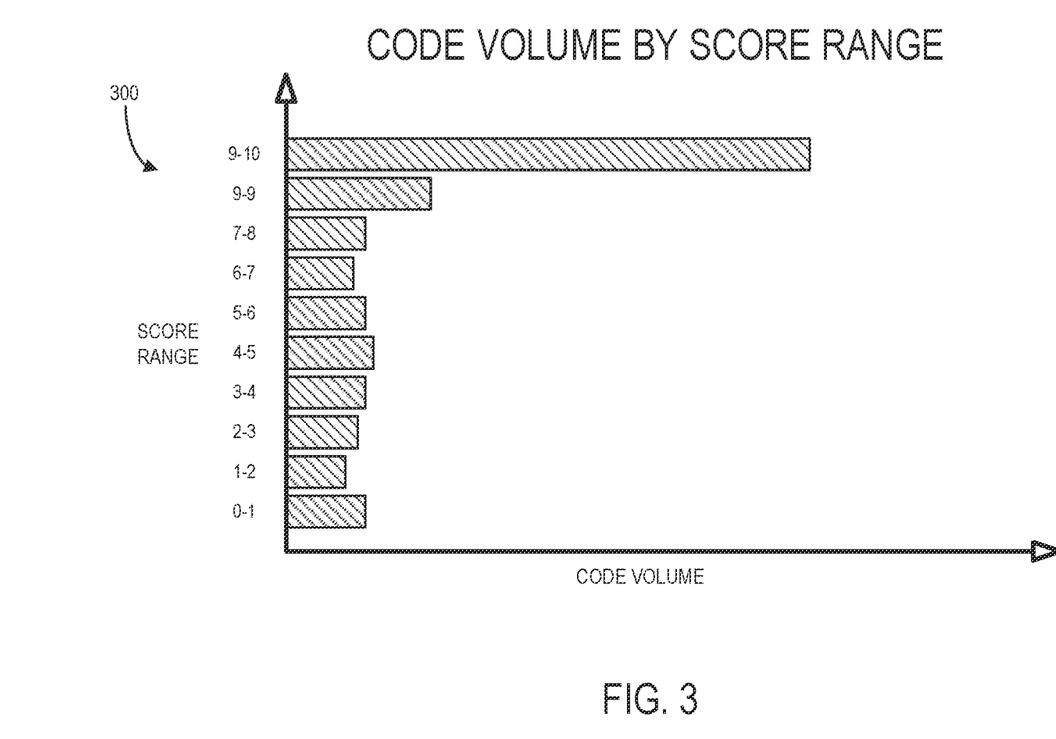
FIG. 3 illustrates ICD volume by score range in accordance with some embodiments.

FIG. 3 illustrates 300 ICD volume by score range in accordance with some embodiments. In particular, the score ranges from 0 (worst likelihood) to 10 (best likelihood). Payment for unrelated ICD codes may account for a substantial amount of annual medical leakage today. According to some embodiments, an ICD decision model mitigates this leakage through ICD transaction automation and decision augmentation. An enterprise may process hundreds of thousands ICD codes annually, and most ICD codes are accepted as related to the claim. According to some embodiments, an ICD decision model may combine the power of predictive models and business rules to automate and augment handler ICD decisions, leading to improved efficiency and accuracy of ICD decisions. The scores may then be translated into one of four recommendations: automatic approve, likely related, unable to recommend, and unlikely related.

Figure 4:
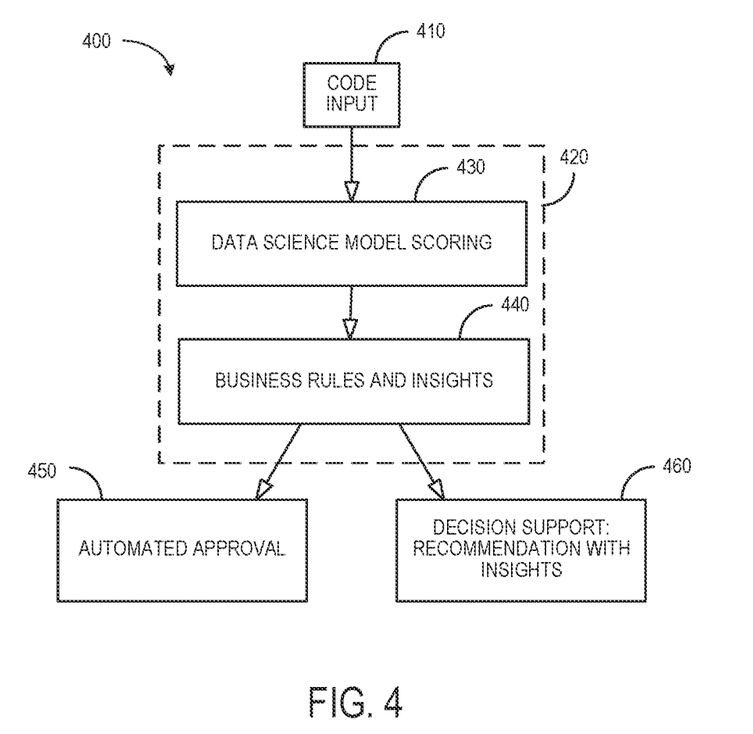
FIG. 4 is an ICD decision model system according to some embodiments.

FIG. 4 is an ICD decision model system 400 according to some embodiments. As shown, a code input 410 is provided to an ICD decision model 420 that includes data science model scoring 430 and business rules and insights 440. The output of the business rules and insights 440 might indicate an automated approval 450 or decision support 460 that includes recommendation with insights. In this way, the system 400 may score each ICD code with a likelihood of acceptance. The ICD decision model combines the power of predictive models and business rules to automate or augment ICD decisions in a substantially real-time response.

Figure 5:
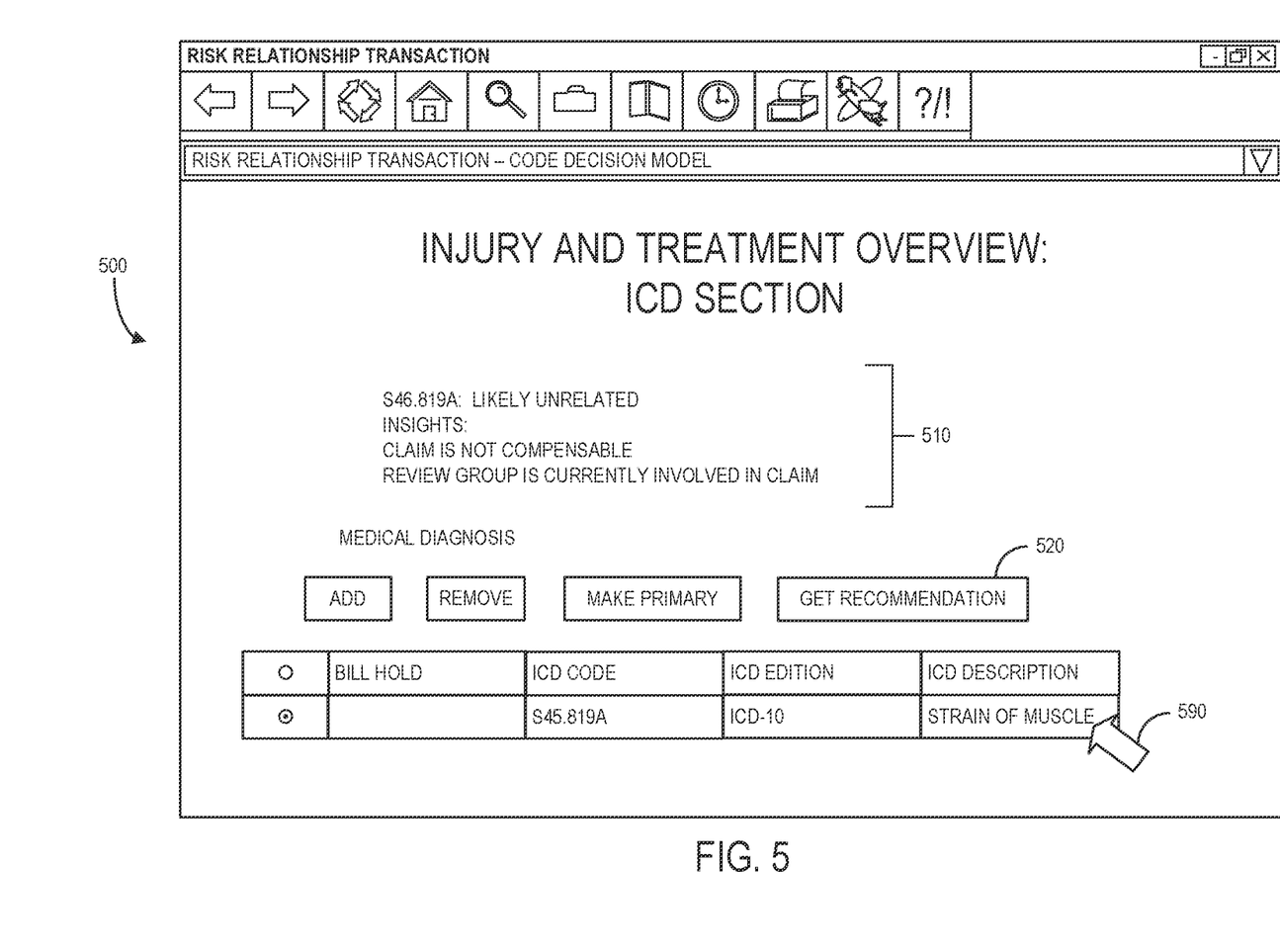
FIG. 5 is an injury and treatment overview display in accordance with some embodiments.

FIG. 5 is an injury and treatment overview display 500 in accordance with some embodiments. The display 500 might provide a summary associated with an ICD code 510, selection icons 520 to add or remove a medical diagnosis, make a diagnosis primary, get a recommendation, etc. According to some embodiments, selection of a diagnosis (e.g., via touch screen or a computer mouse pointer 590) might result in a pop-up window providing additional information (e.g., an indication that the injury is under investigation, is being treated, etc.). According to some embodiments, the display 500, along with the other displays described herein, give a claim handler a high-level, holistic view that aggregates data from various disparate sources in connection with a single workers' compensation insurance claim. Such a view may help the handler process the claim in a more efficient and accurate manner.

Note that embodiments may leverage insights from multiple machine learning assets and claim metrics to give a holistic view of the claim in one place. Moreover, risks of certain aspects of a claim may be calculated by the system which can then provide a "next best action" to a claim handler. In addition, the data visualization of claim activity and risk factors may enable quick orientation to the claim and provides a direction where a claim handler's attention should be focused (and, in some embodiments, a next best action). Further note that embodiments may provide information to help claim handlers determine a course of action (without automatically making any claim decisions).

Figure 6:
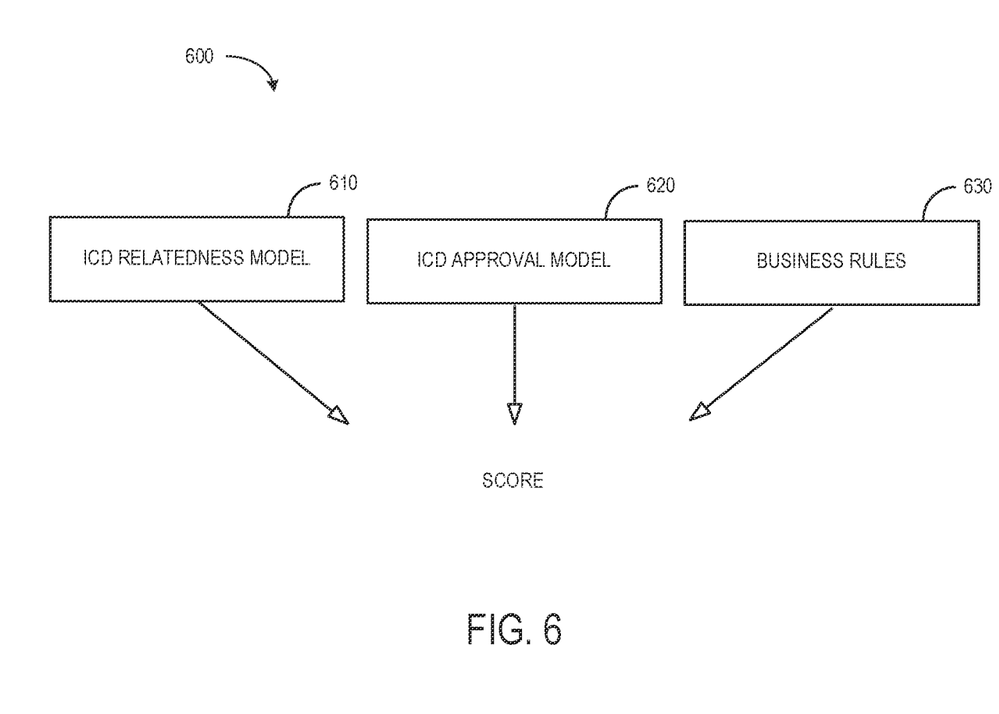
FIG. 6 is a code decision model design according to some embodiments.

FIG. 6 is a code decision model design 600 in accordance with some embodiments. The design 600 may include an ICD relatedness model 610, an ICD approval model 620, and/or business rules 630 that may all contribute to an overall score for a transaction (e.g., a workers' compensation insurance claim transaction). The design may quantify the degree of related-ness among ICD codes. According to some embodiments, a Hierarchical Variable Clustering ("HVC") unsupervised learning technique learns the appropriate level of group homogeneity of ICD codes. The HVC may group two highly-related ICD codes into a small cluster, then continue to group two adjacent clusters into a larger cluster to statistically build an entire hierarchy. With the right number of clusters learned through HVC, the design 600 may the use the K-means variable clustering to quickly group the ICD codes into clusters. This data driven approach might use, for example, hundreds of thousands of historical ICD codes from workers' compensation claims and align them into hundreds of unique clusters.

The output from the ICD relatedness model 610 may become inputs, among other claim variables, into the ICD approval model 620. The ICD approval model 620 might use, for example, a supervised learning technique to predict the likelihood of accepting each ICD code based on a set of variables representing factors related to the injury, claim characteristics and its ICD that influence the ultimate ICD decision.

Some considerations that impact the ICD decision may be more conducive to a business rules 630 approach. For example, if a claim is non-compensable then its ICD codes should likewise be denied. Each ICD code may receive a score from the ICD approval model 620 which is translated to a recommendation based on pre-determined thresholds. The business rules 630 may then be executed after the ICD approval model 620 to drive an array of recommendation shifts based on the type of rule that is triggered.

Figure 7:
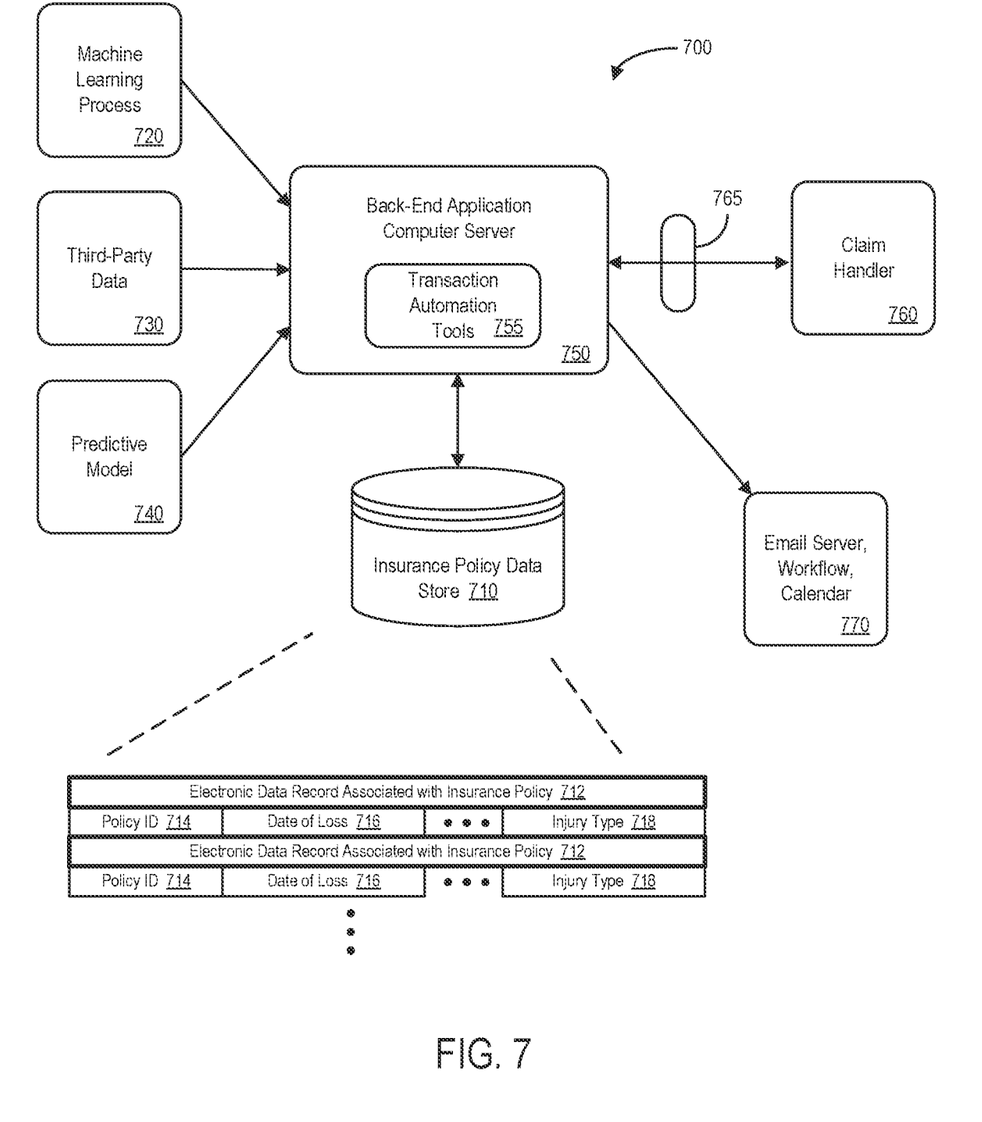
FIG. 7 is a more detailed high-level block diagram of a system in accordance with some embodiments.

FIG. 7 is a more detailed high-level block diagram of a system 700 in accordance with some embodiments. As before, the system 700 includes a back-end application computer 750 server that may access information in an insurance policy data store 710. The back-end application computer server 750 may also retrieve information from a machine learning process 720, a third-party data 730 (e.g., from medical providers or police reports), and/or predictive models 740 in connection with transaction automation tools 755. The back-end application computer server 750 may also exchange information with a claim handler device 760 (e.g., via communication port 765 that might include a firewall) to enable a manual review of an insurance claim transaction. The back-end application computer server 750 might also transmit information directly to an email server, workflow application, and/or calendar application 770 to facilitate automated insurance claim transaction processing.

The back-end application computer server 750 may store information into and/or retrieve information from the insurance policy data store 710. The insurance policy data store 710 might, for example, store electronic records 712 representing a plurality of insurance claims (e.g., resource allocation request transactions), each electronic record having a set of attribute values including an insurance policy identifier 714, a date of loss 716, an injury type 718, etc. According to some embodiments, the system 700 may provide a dashboard view of insurance claim files.

Figure 8:
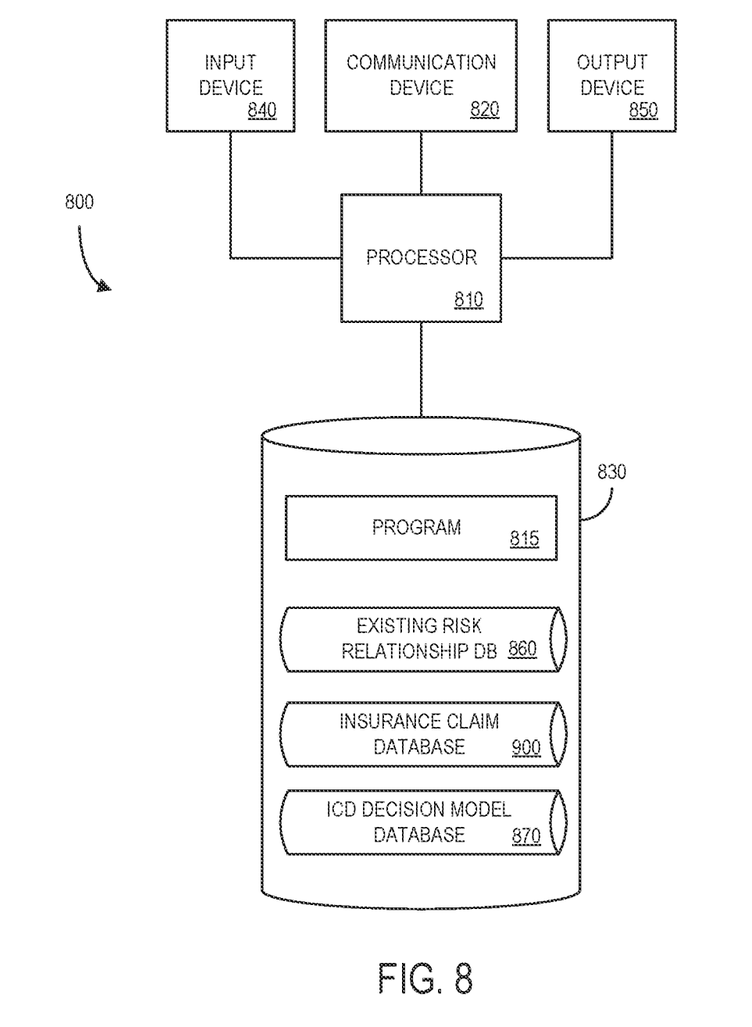
FIG. 8 is a block diagram of an apparatus in accordance with some embodiments of the present invention.

The embodiments described herein may be implemented using any number of different hardware configurations. For example, FIG. 8 illustrates an apparatus 800 that may be, for example, associated with the system 100 described with respect to FIG. 1. The apparatus 800 comprises a processor 810, such as one or more commercially available Central Processing Units ("CPUs") in the form of one-chip microprocessors, coupled to a communication device 820 configured to communicate via communication network (not shown in FIG. 8). The communication device 820 may be used to communicate, for example, with one or more remote administrator computers and or communication devices (e.g., PCs and smartphones). Note that communications exchanged via the communication device 820 may utilize security features, such as those between a public internet user and an internal network of the insurance enterprise. The security features might be associated with, for example, web servers, firewalls, and/or PCI infrastructure. The apparatus 800 further includes an input device 840 (e.g., a mouse and/or keyboard to enter information about an insured, injuries, claim negotiations, etc.) and an output device 850 (e.g., to output reports regarding insurance claim status).

The processor 810 also communicates with a storage device 830. The storage device 830 may comprise any appropriate information storage device, including combinations of magnetic storage devices (e.g., a hard disk drive), optical storage devices, mobile telephones, and/or semiconductor memory devices. The storage device 830 stores a program 815 and/or a resource allocation tool or application for controlling the processor 810. The processor 810 performs instructions of the program 815, and thereby operates in accordance with any of the embodiments described herein. For example, the processor 810 may provide a risk relationship transaction automation tool. A risk relationship data store may contain electronic records representing transactions associated with requested resource allocations between the enterprise and a plurality of entities. The processor 810 may receive an indication of a selected requested resource allocation transaction and retrieve, from the risk relationship data store, the electronic record associated with the selected requested resource allocation transaction. The processor 810 may then execute a code decision model. The processor 810 may also support a graphical interactive user interface display via a distributed communication network, the interactive user interface display providing resource allocation data.

The program 815 may be stored in a compressed, uncompiled and/or encrypted format. The program 815 may furthermore include other program elements, such as an operating system, a database management system, and/or device drivers used by the processor 810 to interface with peripheral devices.

As used herein, information may be "received" by or "transmitted" to, for example: (i) the back-end application computer server 800 from another device; or (ii) a software application or module within the back-end application computer server 800 from another software application, module, or any other source.

In some embodiments (such as shown in FIG. 8), the storage device 830 further stores an existing risk relationship database 860 (e.g., containing insurance policy information), an insurance claim database 900, and an ICD decision model database 870. An example of a database that might be used in connection with the apparatus 800 will now be described in detail with respect to FIG. 9. Note that the database described herein is only an example, and additional and/or different information may be stored therein. Moreover, various databases might be split or combined in accordance with any of the embodiments described herein. For example, the existing risk relationship database 860 and the insurance claim database 900 might be combined and/or linked to each other within the program 815.

Figure 9:
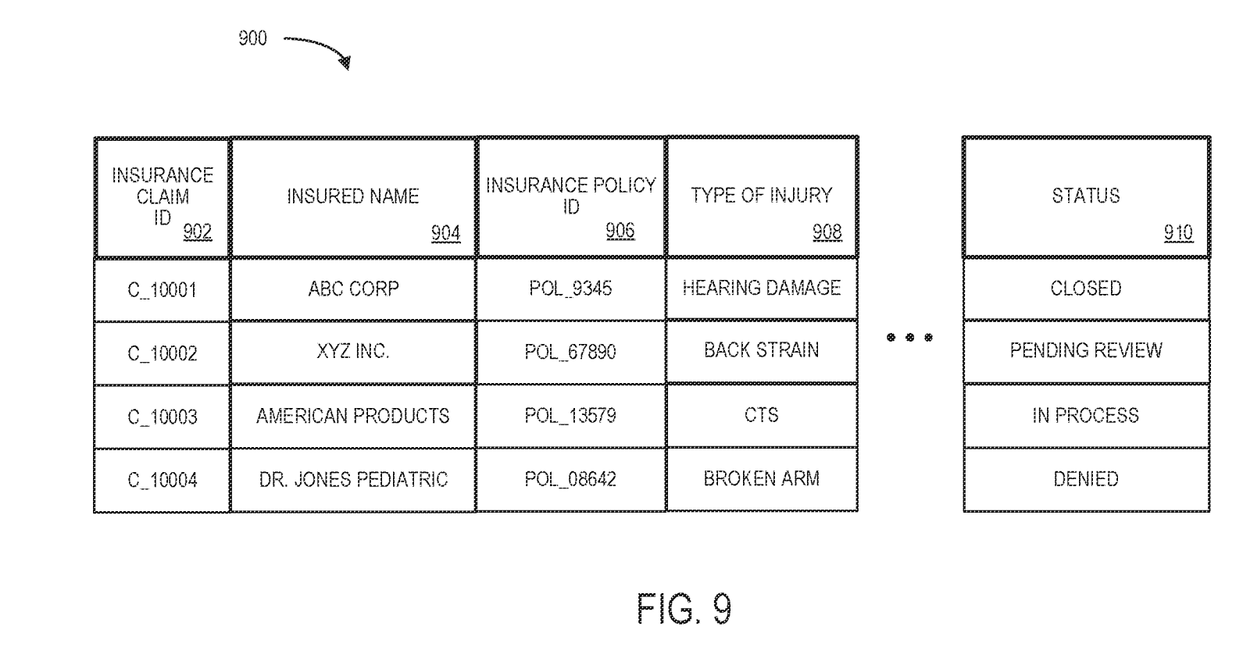
FIG. 9 is a portion of a tabular insurance claim database according to some embodiments.

Referring to FIG. 9, a table is shown that represents the insurance claim database 900 that may be stored at the apparatus 800 according to some embodiments. The table may include, for example, entries associated with insurance claims that have been submitted by claimants. The table may also define fields 902, 904, 906, 908, 910 for each of the entries. The fields 902, 904, 906, 908, 910 may, according to some embodiments, specify: an insurance claim identifier 902, an insured name 904, an insurance policy identifier 906, a type of injury 908, and a status 910. The insurance claim database 900 may be created and updated, for example, based on information electrically received from various operators, administrators, and computer systems, including those associated with an insurer.

The insurance claim identifier 902 may be, for example, a unique alphanumeric code identifying a request for resources (e.g., when an employee working for an insured becomes injured while at work). The insured name 904 might be associated with the owner of insurance policy associated with the identifier 906. The type of injury 908 might indicate when the worker was hurt and might, according to some embodiments, include an ICD code. Note that the insurance claim database 900 will include additional information about each insurance claim (not illustrated in FIG. 9), such as claim handler notes, medical treatment costs, legal negotiations, etc. The status 910 might indicate that the insurance claim is closed, pending review, in process, denied, etc.

Thus, embodiments may provide an automated and efficient way for a risk relationship transaction automation tool to allow faster, more accurate results as compared to traditional approaches. Embodiments may aggregate data from multiple sources and use machine learning algorithms to help claim handlers to quickly recognize which claims might need closer attention. By digesting information, such as medical records, and applying artificial intelligence, embodiments may leverage available data and automate medical treatment judgements, help motivate and influence claimant behavior, etc. The displays may provide a "360" degree view of a claim or customer including aggregated data from many different sources. For example, a claim handler might quickly understand two years of complex claim processing with such an end-to-end view of the data. Note that the data used to render the displays described herein might include data from unstructured sources, such as paragraphs of text from manually created notes, governmental or medical documents, phone call transcripts, etc.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Although specific hardware and data configurations have been described herein, note that any number of other configurations may be provided in accordance with embodiments of the present invention (e.g., some of the information associated with the displays described herein might be implemented as a virtual or augmented reality display and/or the databases described herein may be combined or stored in external systems). Moreover, although embodiments have been described with respect to particular types of insurance policies, embodiments may instead be associated with other types of insurance policies in additional to and/or instead of the policies described herein (e.g., professional liability insurance policies, extreme weather insurance policies, etc.). Similarly, although certain attributes (e.g., values analyzed in connection with resource allocation requests) were described in connection some embodiments herein, other types of attributes might be used instead.

Figure 10:
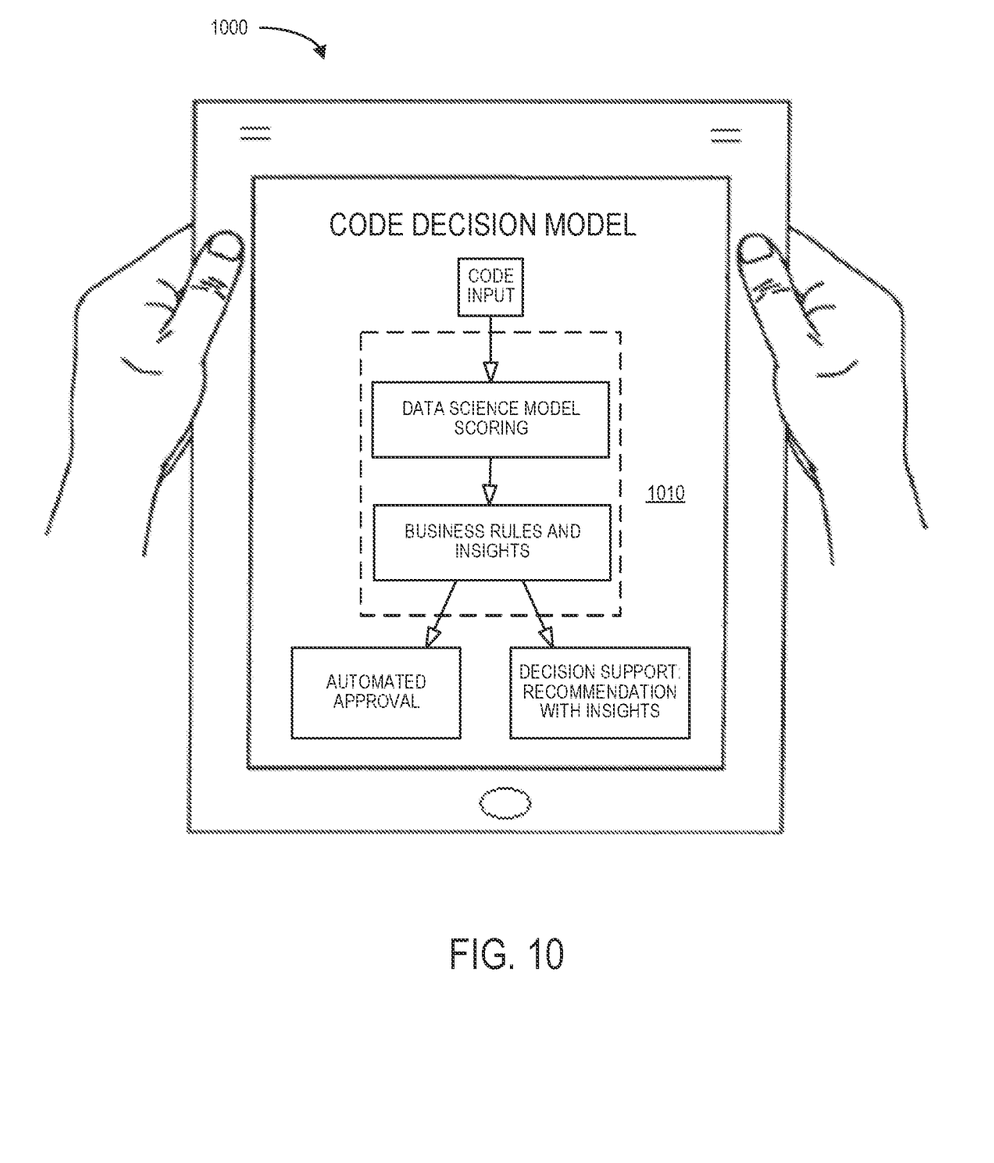
FIG. 10 illustrates a tablet computer displaying a risk relationship resource allocation tool user interface according to some embodiments.

Further, the displays and devices illustrated herein are only provided as examples, and embodiments may be associated with any other types of user interfaces. For example, FIG. 10 illustrates a handheld tablet computer 1000 showing a risk relationship resource allocation tool display 1010 according to some embodiments. The resource allocation tool display 1010 might include user-selectable data that can be selected and/or modified by a user of the handheld computer 1010 to provide information about insurance claim transactions.

Note that the displays described herein might be constantly updated based on new information (e.g., as data is received by the insurer). For example, the displays might be updated in substantially real time or on a periodic basis (e.g., once each night). According to some embodiments, a claim handler might be able to select a particular time in the past and the displays may be updated to reflect the information as it previously existed at that particular time (e.g., what would the claim handler have seen one year ago?).

Figure 11:
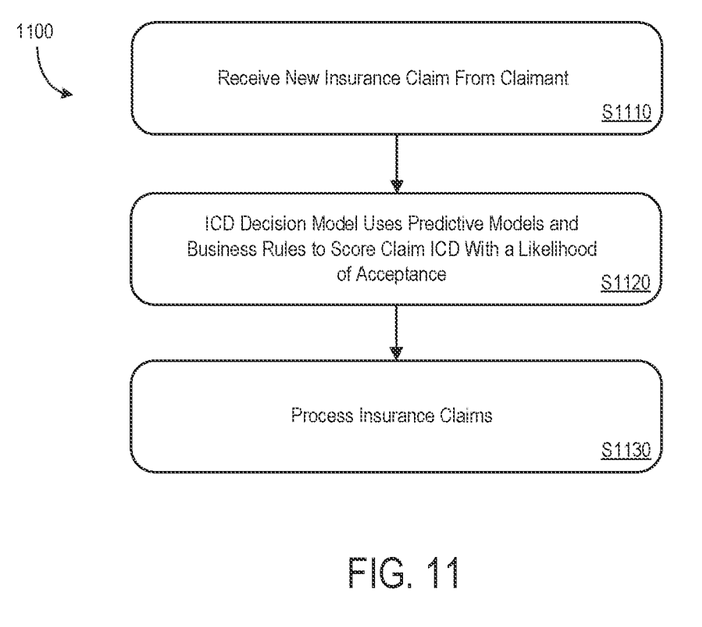
FIG. 11 illustrates an overall process in accordance with some embodiments.

FIG. 11 illustrates an overall business process 1100 in accordance with some embodiments. At S1110, an insurer may receive a new workers' compensation insurance claim from a claimant. This information may be collected from various sources, including medical records, an incident report, etc. At S1120, an ICD model may use predictive models and business rules to score claim ICD code with a likelihood of acceptance. The insurer may then process the insurance claim as directed by the claim handler (e.g., by approving medical procedures or otherwise recommending a medical treatment, implementing a return-to-work strategy, etc.) at S1130.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed:

1. A system to provide a risk relationship resource allocation tool via a back-end application computer server of an enterprise, comprising:
   (a) a risk relationship data store containing electronic records that represent a plurality of transactions associated with requested resource allocations between the enterprise and a plurality of entities, wherein each electronic record includes an electronic record identifier and at least one code representing a medical condition;
   (b) the back-end application computer server, coupled to the risk relationship data store, programmed to:
   (i) receive an indication of a selected requested resource allocation transaction between the enterprise and an entity;
   (ii) retrieve, from the risk relationship data store, the electronic record associated with the selected requested resource allocation transaction, including the at least one code representing a medical condition;
   (iii) execute a predictive model trained with a machine learning process and business rules based on the at least one code to generate a likelihood of acceptance score for the selected requested resource allocation transaction, wherein the likelihood of acceptance score predicts a likelihood the at least one code is approved;
   (iv) assign the selected requested resource allocation transaction to a recommendation category based on the likelihood of acceptance score, wherein the assigned recommendation category represents automatic approval of the code thereby reducing a number of electronic messages being transmitted via a distributed communication network;

(v) automatically route the selected requested resource allocation transaction to a claim handler device based on the assigned recommendation category;

(vi) generate a "next best action" for the selected requested resource allocation transaction based on output of multiple machine learning assets;

(vii) transmit the "next best action", wherein a summary associated with the code and the "next best action" is displayed on a user interface of the claim handler device;

(viii) generate a pop-up window on the user interface in response to selection of the code, wherein the pop-up window provides additional information that is not available without the selection to reduce a number of electronic messages transmitted via the distributed communication network; and (c) a communication port coupled to the back-end application computer server to facilitate a transmission of data with a remote device to support a graphical interactive user interface display and the distributed communication network, the interactive user interface display providing resource allocation data including the likelihood of acceptance score and the recommendation category.

2. The system of claim 1, wherein the at least one medical code is associated with an international classification of diseases code.

3. The system of claim 2, wherein the selected requested resource allocation transaction is associated with a workers' compensation insurance claim, and the predictive model is associated with data science model scoring.

4. The system of claim 3, wherein the assigned recommendation category comprises one of: (i) likely related, (ii) unable to recommend, and (iii) unlikely related.

5. The system of claim 3, wherein the data science model scoring utilizes a hierarchical variable clustering process and unsupervised learning based on historical insurance claim results.

6. The system of claim 1 wherein the "next best action" is transmitted via at least one of an email server, a calendar function, and a workflow application coupled to the back-end application computer server, and at least one of which receives at least one of: an automatically approved selected requested resource allocation transaction and the generated "next best action".

7. A computerized method to provide a risk relationship resource allocation tool via a back-end application computer server of an enterprise, comprising:

receiving, at the back-end application computer server, an indication of a selected requested resource allocation transaction between the enterprise and an entity;

retrieving, from a risk relationship data store, an electronic record associated with the selected requested resource allocation transaction, including at least one code representing a medical condition, wherein the risk relationship data store contains electronic records that represent a plurality of transactions associated with requested resource allocations between the enterprise and a plurality of entities, each electronic record including an electronic record identifier and the at least one code representing a medical condition;

executing a predictive model trained with a machine learning process and business rules based on the at least one code to generate a likelihood of acceptance score for the selected requested resource allocation transaction, wherein the likelihood of acceptance score a likelihood the at least one code is approved;

assigning the selected requested resource allocation transaction to a recommendation category based on the likelihood of acceptance score, wherein the assigned recommendation category represents automatic approval of the code thereby reducing a number of electronic messages being transmitted via a distributed communication network;

automatically routing the selected requested resource allocation transaction to a claim handler device based on the assigned category;

generating a "next best action" for the selected requested resource allocation transaction based on output of multiple machine learning assets;

transmitting the "next best action", wherein a summary associated with the code and the "next best action" is displayed on a user interface of the claim handler device; and generating a pop-up window on the user interface in response to selection of the code, wherein the pop-up window provides additional information that is not available without the selection, to reduce a number of electronic messages transmitted via the distributed communication network.

8. The method of claim 7, wherein the at least one medical code is associated with an international classification of diseases code.

9. The method of claim 8, wherein the selected requested resource allocation transaction is associated with a workers' compensation insurance claim, and the predictive model is associated with data science model scoring.

10. The method of claim 9, wherein the assigned recommendation category comprises one of: (i) likely related, (ii) unable to recommend, and (iii) unlikely related.

11. The method of claim 9, wherein the data science model scoring utilizes a hierarchical variable clustering process and unsupervised learning based on historical insurance claim results.

12. The method of claim 7, wherein the "next best action" is transmitted via at least one of an email server, a calendar function, and a workflow application.

13. A non-transitory, computer-readable medium storing instructions, that, when executed by a processor, cause the processor to perform a method to provide a risk relationship resource allocation tool via a back-end application computer server of an enterprise, the method comprising:

receiving, at the back-end application computer server, an indication of a selected requested resource allocation transaction between the enterprise and an entity;

retrieving, from a risk relationship data store, an electronic record associated with the selected requested resource allocation transaction, including at least one code representing a medical condition, wherein the risk relationship data store contains electronic records that represent a plurality of transactions associated with requested resource allocations between the enterprise and a plurality of entities, each electronic record including an electronic record identifier and at least one code representing a medical condition;

executing a predictive model trained with a machine learning process and business rules based on the at least one code to generate a likelihood of acceptance score for the selected requested resource allocation transaction, wherein the likelihood of acceptance score predicts a likelihood the at least one code is approved;

assigning the selected requested resource allocation transaction to a recommendation category based on the likelihood of acceptance score, wherein the assigned recommendation category represents automatic approval of the code thereby reducing a number of electronic messages being transmitted via a distributed communication network;

automatically routing the selected requested resource allocation transaction to a claim handler based on the assigned category;

generating a "next best action" for the selected requested resource allocation transaction based on output of multiple machine learning assets;

transmitting the "next best action", wherein a summary associated with the code and the "next best action" is displayed on a user interface of a claim handler device; and generating a pop-up window on the user interface in response to selection of the code, wherein the pop-up window provides additional information that is not available without the selection to reduce a number of electronic messages transmitted via the distributed communication network.

14. The medium of claim 13, wherein the at least one medical code is associated with an international classification of diseases code.

15. The medium of claim 14, wherein the selected requested resource allocation transaction is associated with a workers' compensation insurance claim, and the predictive model is associated with data science model scoring.

16. The medium of claim 15, wherein the assigned recommendation category comprises one of: (i) likely related, (ii) unable to recommend, and (iii) unlikely related.

17. The medium of claim 15, wherein the data science model scoring utilizes a hierarchical variable clustering process and unsupervised learning based on historical insurance claim results.

18. The medium of claim 13, wherein the "next best action" is transmitted via at least one of an email server, a calendar function, and a workflow application.

* * * * *